(12) United States Patent
Hoffman (10) Patent No.: US 10,039,693 B1
(45) Date of Patent: Aug. 7, 2018

(54) ACUPRESSURE APPARATUS

(71) Applicant: Ned Hoffman, Sebastopol, CA (US)

(72) Inventor: Ned Hoffman, Sebastopol, CA (US)

(73) Assignee: Holden Properties, LLC, Reno, NV (US)

( * ) Notice: Subject to any disclaimer, the term of this patent is extended or adjusted under 35 U.S.C. 154(b) by 0 days.

(21) Appl. No.: 15/191,782

(22) Filed: Jun. 24, 2016

Related U.S. Application Data (63) Continuation of application No. 14/083,606, filed on Nov. 19, 2013, now abandoned.

(60) Provisional application No. 61/733,381, filed on Dec. 4, 2012.

(51) Int. Cl.
| | | |
|---|---|---|
| *A61B 17/00* | (2006.01) | |
| *A61H 39/04* | (2006.01) | |
| *A61F 9/04* | (2006.01) | |
| *A61F 11/08* | (2006.01) | |

(52) U.S. Cl.
CPC ............... *A61H 39/04* (2013.01); *A61F 9/04* (2013.01); *A61F 11/08* (2013.01); *A61H 2201/0157* (2013.01); *A61H 2201/02* (2013.01); *A61H 2201/102* (2013.01); *A61H 2201/1604* (2013.01); *A61H 2201/165* (2013.01); *A61H 2205/023* (2013.01)

(58) Field of Classification Search
CPC .... A61B 17/1325; A61H 39/00; A61H 39/04; A61H 39/06; A61H 2201/00; A61H 2201/01; A61H 2201/02; A61H 2201/16; A61H 2201/0207; A61H 2201/0214; A61H 2201/0221; A61H 2201/10; A61H 2201/102; A61H 2201/1602; A61H 2201/165; A61H 2201/1657; A61H 2201/0157; A61H 2201/0192; A61H 2201/1604; A61H 2205/00; A61H 2205/02; A61H 2205/022; A61H 2205/025; A61F 9/04; A61F 9/045; A61F 11/08

USPC .................................... 606/204, 204.15
See application file for complete search history.

(56) References Cited

U.S. PATENT DOCUMENTS

| | | | | |
|---|---|---|---|---|
| 6,554,787 | B1 * | 4/2003 | Griffin | A61F 7/02 601/70 |
| 2002/0007195 | A1 * | 1/2002 | Wexler | A61F 5/30 606/204.15 |
| 2005/0222608 | A1 * | 10/2005 | Hou | A61H 39/04 606/204 |
| 2010/0113991 | A1 * | 5/2010 | Wu | A61H 7/006 601/46 |
| 2013/0253257 | A1 * | 9/2013 | Kalhory | A61F 7/02 600/27 |

* cited by examiner

*Primary Examiner* — Melanie Tyson
(74) *Attorney, Agent, or Firm* — Antonio Papageorgiou; Meister Seelig & Fein LLP (57) ABSTRACT

An acupressure apparatus including a manually adjustable head strap, with a flexible material, extending around the circumference of a user's head, and which can be manually adjusted using any of the following: a hook segment; a loop segment; a button; a buttonhole; a snap; and a snap receptacle. The acupressure apparatus includes a rigid protrusion with a rigid material formed into an essentially domed shape. The protrusion can be affixed to a point of the head strap such that the dome faces the user's glabella. When the user manually adjusts the length of the head strap, the rigid protrusion applies pressure on the user's glabella.

10 Claims, 6 Drawing Sheets

ACUPRESSURE APPARATUS

CROSS-REFERENCE TO RELATED APPLICATION

This utility patent application is a continuation of utility patent application Ser. No. 14/083,606, filed on Nov. 19, 2013, which claims the benefit of provisional patent application Ser. No. 61/733,381, filed on Dec. 4, 2012, all of which are incorporated herein by reference.

FIELD OF THE INVENTION

The present invention relates to an acupressure apparatus, and more specifically to a head strap which has an embedded rigid protrusion which applied pressure to an epidermal point on the user's glabella, or Yintang pressure point.

BACKGROUND OF THE INVENTION

The channels, or meridians, on the body used for acupressure make up a complex network along which energy, or qi, travels. Acupressure points are located on areas where the qi flows closer to the surface of the body. In addition to points along specific channels, there are a number of extra points located outside of the specific pathways. One of these extra points is a particularly special one, called Yintang or Third-Eye. Its corollary location in allopathic medicine is known as the glabella. More specifically, the glabella, in humans, is the space between the eyebrows and above the nose. It is slightly elevated, and joins the two superciliary ridges. The most common uses for Yintang are to treat frontal headache, nasal congestion and sinus problems, stress, insomnia, hypertension, and anxiety. Research on the benefits of Yintang include a 2005 study published in the journal *Medical Acupressure* entitled "Shenting and Yintang: Quantification Of Cerebral Effects Of Acupressure, Manual Acupressure, and Laserneedle Acupressure Using High-Tech Neuromonitoring Methods," by Gerhard Litscher, MDsc. The study was about the electroencephalographic similarities of acupressure induced sedation and general anesthesia, as assessed by bispectral index and spectral edge frequency. Among other conclusions, the study result showed similarities measured in the human brain both under sedation using Yintang and sedation using anesthesia.

Traditionally, an individual needs to undertake the time, expense and inconvenience of hiring a massage specialist to administer the Yintang acupressure point on him or her, through the massage therapist's use of their fingers and hands. Alternatively, the individual must attempt to self-administer application of the Yintang acupressure point, by using his or her own fingers and hands, which is difficult and uncomfortable to do. Therefore, there is a strong need for a more efficient, effective, and comfortable way to administer Yintang acupressure on an epidermal point of the user's glabella, which does not require either the individual or a massage specialist to undertake manual message.

The present invention addresses these needs, wherein still further objectives and advantages of this invention will become apparent from a consideration of the ensuing description and drawings.

SUMMARY OF THE INVENTION

The present invention satisfies these needs by providing a Yintang acupressure apparatus or assembly.

In an embodiment of the invention, an acupressure apparatus comprises: a) A manually adjustable head strap, comprising: a flexible material, and: measuring essentially 600 millimeters in length, essentially 30 millimeters in width, and essentially 3 millimeters in thickness, wherein the length of the head strap can be manually adjusted to accommodate the circumferential dimensions of a user's head as measured from the user's forehead and going all the way around the head along the "x" axis, said manual adjustability comprising any of the following: a hook segment; a loop segment; a button; a buttonhole; a snap; and a snap receptacle; and, b) An essentially rigid protrusion comprising: an essentially rigid material formed into an essentially domed shape, and; measuring essentially 30 millimeters in diameter, essentially 11 millimeters in height, said protrusion being affixed to a point of the head strap such that the apex of the dome faces an epidermal point essentially on the user's glabella, Whereby, upon manually adjusting the length of the head strap, the essentially rigid protrusion applies pressure on the user's glabella.

In another embodiment of the invention, an acupressure apparatus comprises: a) A manually adjustable head strap, comprising: a flexible material, and: measuring essentially 600 millimeters in length, essentially 30 millimeters in width, and essentially 3 millimeters in thickness, wherein the length of the head strap can be manually adjusted to accommodate the circumferential dimensions of a user's head as measured from the user's forehead and going all the way around the head along the "x" axis, said manual adjustability comprising any of the following: a hook segment; a loop segment; a button; a buttonhole; a snap; and a snap receptacle; and, b) A semi-flexible protrusion comprising: a semi-flexible material formed into an essentially domed shape, and; measuring essentially 30 millimeters in diameter, essentially 11 millimeters in height, said protrusion being affixed to a point of the head strap such that the apex of the dome faces an epidermal point essentially on the user's glabella, Whereby, upon manually adjusting the length of the head strap, the rigid protrusion applies pressure on the user's glabella.

In another embodiment of the invention, the glabella comprises an epidermal point on the user's forehead located essentially just above the nose bridge and essentially midway between the medial ends of the user's two eyebrows.

In another embodiment of the invention, the essentially rigid protrusion further comprises a hollowed core, wherein a non-rigid material is placed, said material being operable to retain heat or cold for essentially at least 2 minutes.

In another embodiment of the invention, the essentially rigid protrusion further comprises an essentially rigid, temperature-sensitive material operable to retain heat or cold for essentially at least 2 minutes.

In another embodiment of the invention, the acupressure apparatus further comprises an eye cover comprising a flexible, light-occluding material, said eye cover measuring essentially 225 millimeters in length, essentially 90 millimeters in width at the points covering each eye, and essentially 3 millimeters in thickness, said eye cover being affixed to the head strap.

In another embodiment of the invention, the eye cover is removeable and further comprises any of the following: a hook segment; a loop segment; a button; a buttonhole; a snap; and a snap receptacle.

In another embodiment of the invention, the head strap further comprises at least one pocket operable to receive any of the following: an earplug, and; an aromatic material.

It will be appreciated that the invention disclosed herein through illustrative embodiments may suitably be practiced in the absence of any element which is not specifically disclosed herein, particularly in a preferred embodiment.

These and other advantages of the invention will become more fully apparent when the following detailed description of the invention is read in conjunction with the accompanying drawings.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

GLOSSARY

The following terms are defined herein under:

The article "A", or "An", means: "at least one" of anything to which it refers, such as a component, feature, element, apparatus, piece, or the like of the invention. For example, "a pocket" means "at least one pocket".

The term "Plurality", means: "two or more" of anything to which it refers. For example, "plurality of pockets" means "two or more pockets".

The term "Comprising" (or "Comprises"), means: "including, but not limited to" any one thing to which it refers, inclusive of meaning singularly, in combination, in any combination, and/or in any order. For example, "comprises any of the following: a head strap, and; a buckle" means "at least one of a head strap and/or a buckle", and/or "any combination of at least one head strap, and/or; at least one buckle", while not being limited to any particular combination or any particular number of each item listed.

The term "Essentially", means, and may be substituted for, any of the following equivalent terms: "approximately", "almost", "nearly", and/or "about", with respect to any dimensions related thereto.

DETAILED DESCRIPTION OF THE INVENTION

The present invention may be described herein in terms of various functional elements, or components, as depicted in the attached drawings, configurations and described embodiments. It should be appreciated that such functional elements may be realized by any number of similar elements configured according to this invention to perform the specified functions. Thus, it should be appreciated that the particular implementations shown and described herein are illustrative of the invention and its preferred mode and are not intended to otherwise limit the scope of the present invention in any way. Indeed, for the sake of brevity, conventional elements of a structure, device, or design may not be described in detail herein. Furthermore, the various figures contained herein are intended to represent illustrative functional embodiments of the invention, and that many alternative or equivalent configurations, elements, and structures are intended to be within the scope of the present invention. It should further be noted that the order of the elements in the attached drawings, specification and claims are not intended as limitations and the drawings, specification and claims may be configured in other orders without deviating from the scope and spirit of the present invention.

In the following detailed description of a preferred embodiments, reference may be made to the accompanying drawings, which form a part hereof, and within which are shown by way of illustration specific embodiments by which the invention may be practiced. It is to be understood that other embodiments may be utilized and structural changes may be made without departing from the scope of the invention.

It is noted that the embodiments of the acupressure apparatus described herein below in detail for exemplary purposes, are of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

The Acupressure Apparatus 26 comprises a plurality, but not necessarily all, of the following components, in any combination and/or in any amount, depending on which embodiment of the Acupressure Apparatus 26 is being described:

Head Strap 1
Head Strap Extension Affixing Material 1a
Eye Cover 2
Pocket Opening 3
Pocket for: Ear Plugs, or Aromatic Material 3a
Eye Cover Removeably Attachable Affixing Material 4
Head Strap Removeably Affixing Material 4a
Buckle 5
Rigid Protrusion (or Yintang Rigid Protrusion) 6
Aromatic Material (or Aromatic Compound) 7
Glabella (or Yintang Pressure Point or Third-Eye) 8
Ear Plugs 9
Protrusion-Securing Pocket (or Protrusion-Securing Mesh) 11

Figure 1:
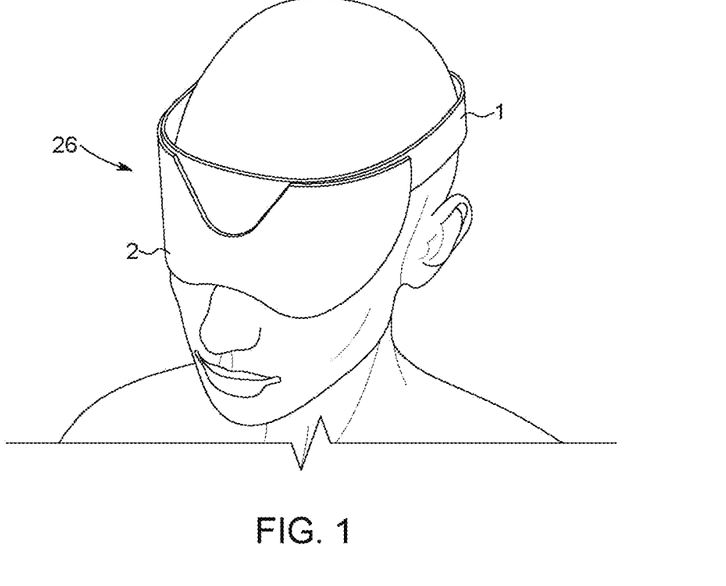
FIG. 1 is illustrative of an embodiment of the invention, including the eye cover, as worn by a user.

FIG. 1 shows an illustrative embodiment of the Acupressure Apparatus 26 as worn by a user, with the Head Strap 1 and the Eye Cover 2.

Figure 2:
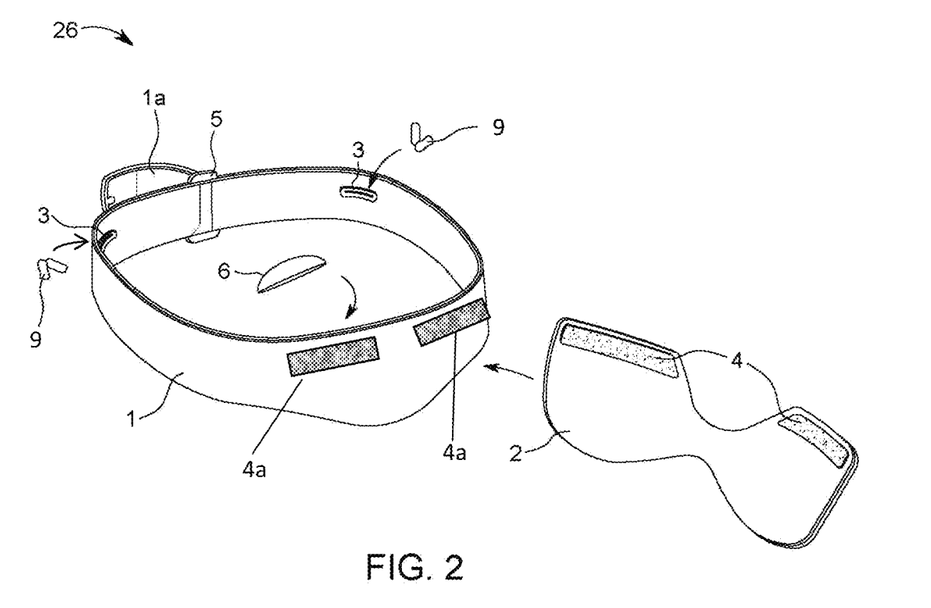
FIG. 2 is illustrative of an embodiment of the invention, including the rigid protrusion, the eye cover, and pockets for ear plugs.

FIG. 2 shows an illustrative embodiment of the Acupressure Apparatus 26 with the Rigid Protrusion 6 shown as it would be positioned to interface with the user's Glabella 8 on the interior side of the Head Strap 1. Here, there are a plurality of Pockets 3 for Ear Plugs 9, and a Buckle 5 for manually adjustably the length of the Head Strap 1 to accommodate the circumferential dimension of a user's head. After the length of the Head Strap 1 has been adjusted, it can be affixed in place with the Head Strap Extension Affixing Material 1a, which is designed to adhere to another part of the Head Strap 1. This Head Strap Extension Affixing Material 1a may include any of the following: a hook segment (such as Velcro®); a loop segment (such as Velcro®); a button; a buttonhole; a snap; and a snap receptacle. The Eye Cover 2 is this embodiment is removeably attachable to the Head Strap 1 via Eye Cover Removeably Attachable Affixing Material 4. This Eye Cover Removeably Attachable Affixing Material 4 may include any of the following: a hook segment (such as Velcro®); a loop segment (such as Velcro®); a button; a buttonhole; a snap; and a snap receptacle.

Figure 3:
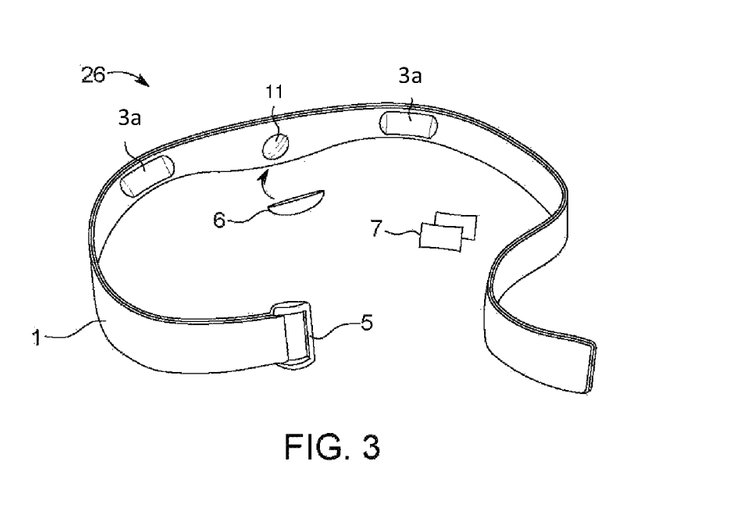
FIG. 3 is illustrative of an embodiment of the invention, including the rigid protrusion and pockets for aromatic material.

FIG. 3 is illustrative of an embodiment of the Acupressure Apparatus 26, as seen from a partially interior perspective where the Head Strap 1 interfaces with the user's epidermal Glabella 8 with the Rigid Protrusion 6 and its corresponding Pocket for Rigid Protrusion 3a. The Aromatic Material 7 is shown with its corresponding Pocket for Aromatic Material 3a. Head Strap Extension Affixing Material 1a is pulled through the Buckle 5 and removeably attaches to another part (not shown) of the Head Strap 1.

Figure 4:
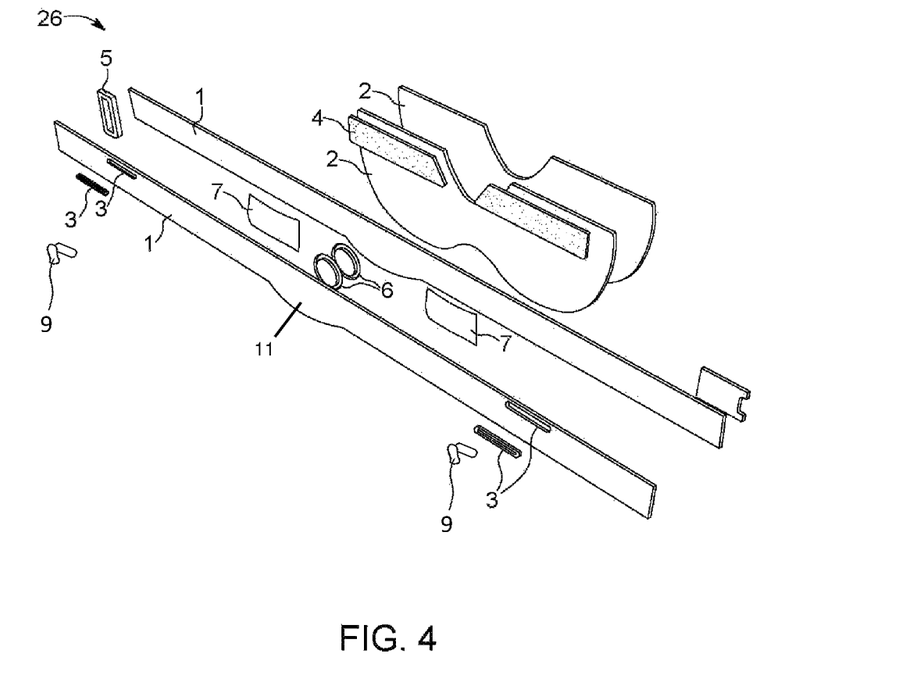
FIG. 4 and FIG. 4A are illustrative of embodiments of the invention, shown in an exploded perspective, including the rigid protrusion, the removeably attachable eye cover, and pockets for ear plugs and aromatic material.

FIG. 4 is illustrative of an embodiment of the Acupressure Apparatus 26, shown here in an exploded view. The Eye Cover 2 includes Eye Cover Removeably Attachable Affixing Material 4 which mates with a part (not shown) of the Head Strap 1. Here, the Rigid Protrusion 6 is shown here as two mating pieces, together encasing a hollow core wherein a non-rigid material is placed, said material being operable to retain heat or cold for essentially at least 2 minutes.

Figure 4A:
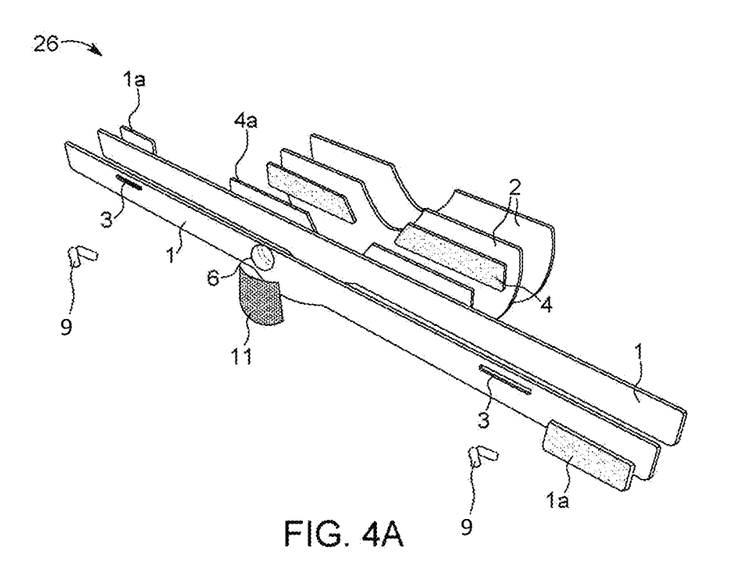

FIG. 4A is illustrative of an embodiment of the Acupressure Apparatus 26, shown here in an exploded view. The Eye Cover 2 includes Eye Cover Removeably Attachable Affixing Material 4 which mates with Head Strap Removeably Affixing Material 4a of the Head Strap 1. Here, the Rigid Protrusion 6 is shown here as one piece, comprising temperature-sensitive material operable to retain heat or cold for essentially at least 2 minutes. Also shown is the Protrusion-Securing Mesh 11, which adheres the Rigid Protrusion 6 to Head Strap 1, and which comprises breathable material through which the heated or cooled Rigid Protrusion 6 can radiate or transmit heat or cool, respectively, to the user's Glabella (or Yintang Pressure Point or Third-Eye) 8 (not shown). In one embodiment, the Protrusion-Securing Mesh 11 has an opening through which the Rigid Protrusion 6 can be inserted or removed, so that the Rigid-Protrusion can be heated (e.g., in a microwave oven) or cooled (e.g., in a freezer) separate from the Acupressure Apparatus 26.

Figure 5A:
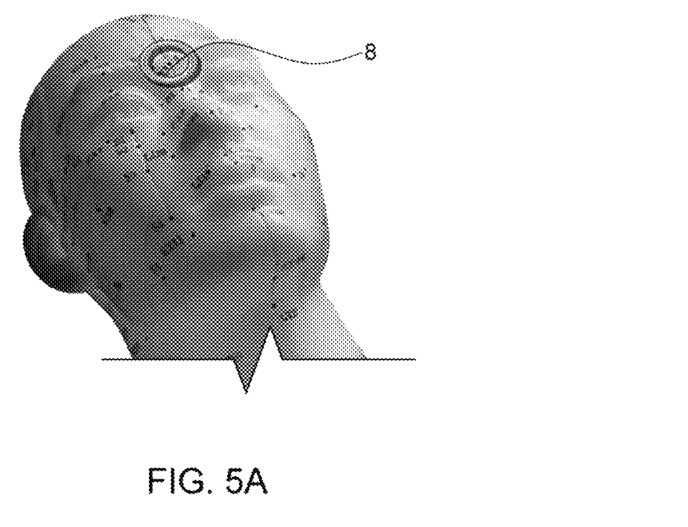
FIG. 5A and FIG. 5B show the epidermal positioning of the glabella (or Yingtang pressure point) on the user's forehead.
Figure 5B:
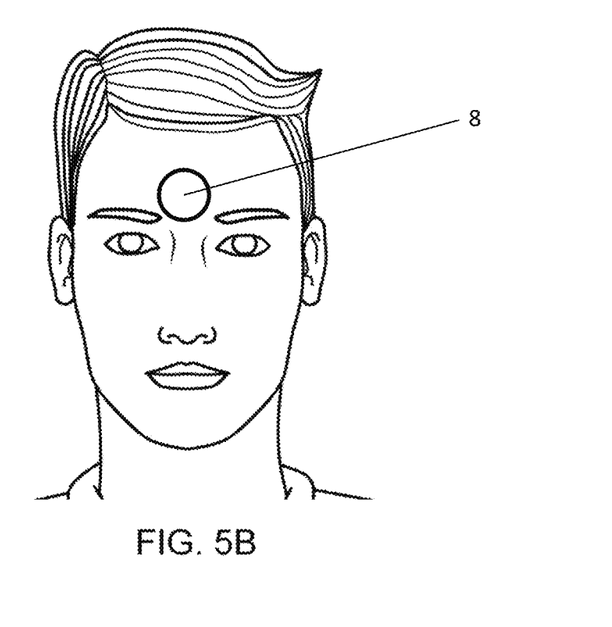

FIG. 5A and FIG. 5B are illustrative of the epidermal placement of the Glabella 9 on a user's forehead.

From the foregoing, it will be appreciated how the invention provides an improved acupressure apparatus.

Further, the improved acupressure apparatus provides an improved means for administering Yintang acupressure positioned on an epidermal point of the user's glabella.

Although the description above contains many specificities, these should not be construed as limiting the scope of the invention but as merely providing illustrations of some of the presently illustrated embodiments of this invention. Thus the scope of this invention should be considered in light of the appended claims and their legal equivalents.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

It is understood that the preceding description is given merely by way of illustration and not in limitation of the invention and that various modifications may be made thereto without departing from the spirit of the invention as claimed.

Although the invention has been described with respect to a particular structure for its use, it will be appreciated that various modifications of the structure are possible without departing from the invention, which is defined by the claims set forth below. For example, the invention can be practiced without any one of its elements, or without any plurality of its elements, and said embodiment(s) are incorporated within the scope of the invention.

What is claimed is:

1. An acupressure apparatus comprising:
   a) A manually adjustable head strap, comprising: a flexible material, and; wherein a length of the head strap can be manually adjusted to accommodate the circumferential dimensions of a user's head as measured from the user's forehead and going all the way around the head along the "x" axis, said manual adjustability comprising any of the following: a hook segment; a loop segment; a button; a buttonhole; a snap; and a snap receptacle; and,
   b) An essentially rigid protrusion formed into an essentially domed shape and comprising a hollowed core, wherein a non-rigid material is placed, said material being operable to retain heat or cold, wherein said protrusion is removeably adherable via a protrusion-securing mesh to a point of the head strap such that an apex of the dome faces an epidermal point essentially on the user's glabella,
   Whereby, upon manually adjusting the length of the head strap, the essentially rigid protrusion applies pressure on the user's glabella.

2. The acupressure apparatus of claim 1, wherein the glabella comprises an epidermal point on the user's forehead located essentially just above the nose bridge and essentially midway between the medial ends of the user's two eyebrows.

3. The acupressure apparatus of claim 1, wherein the protrusion-securing mesh comprises: breathable material through which the heated or cooled essentially rigid protrusion can transmit heat or cool to the user's glabella, and; an opening through which the essentially rigid protrusion can be inserted or removed.

4. The acupressure apparatus of claim 1, further comprising an eye cover comprising a flexible, light-occluding material, said eye cover being removeably affixable to the head strap.

5. The acupressure apparatus of claim 4, wherein the eye cover further comprises any of the following: a hook segment; a loop segment; a button; a buttonhole; a snap; and a snap receptacle.

6. The acupressure apparatus of claim 4, wherein the eye cover measures essentially 225 millimeters in length, essentially 90 millimeters in width at the points covering each eye, and essentially 3 millimeters in thickness.

7. The apparatus of claim 1, wherein the head strap further comprises at least one pocket operable to receive any of the following: an earplug, and; an aromatic material.

8. The acupressure apparatus of claim 1, further comprising at least one of the following: a) the adjustable head strap measures essentially 600 millimeters in length, essentially 30 millimeters in width, and essentially 3 millimeters in thickness; b) the essentially rigid protrusion measures essentially 30 millimeters in diameter, and essentially 11 millimeters in height.

9. An acupressure apparatus comprising:
a) A manually adjustable head strap, comprising: a flexible material, and; wherein a length of the head strap can be manually adjusted to accommodate the circumferential dimensions of a user's head as measured from the user's forehead and going all the way around the head along the "x" axis, said manual adjustability comprising any of the following: a hook segment; a loop segment; a button; a buttonhole; a snap; and a snap receptacle;
b) An essentially rigid protrusion comprising: an essentially rigid material formed into an essentially domed shape; a hollowed core, wherein a non-rigid material is placed, said material being operable to retain heat or cold, and; said protrusion being affixed to a point of the head strap such that an apex of the dome faces an epidermal point essentially on the user's glabella; and,
c) An eye cover comprising a flexible, light-occluding material, said eye cover being removeably affixable to the head strap,
Whereby, upon manually adjusting the length of the head strap, the essentially rigid protrusion applies pressure on the user's glabella.

10. An acupressure apparatus comprising:
a) A manually adjustable head strap, comprising: a flexible material, and; wherein a length of the head strap can be manually adjusted to accommodate the circumferential dimensions of a user's head as measured from the user's forehead and going all the way around the head along the "x" axis, said manual adjustability comprising any of the following: mating hook and loop segments; mating buttons and buttonholes; snaps and snap receptacles, and; a buckle;
b) An essentially rigid protrusion comprising: an essentially rigid material formed into an essentially domed shape; a hollowed core, wherein a non-rigid material is placed, said material being operable to retain heat or cold, and; said protrusion being affixed to a point of the head strap such that an apex of the dome faces an epidermal point essentially on the user's glabella; and,
c) At least one pocket within the head strap, said pocket operable to receive any of the following: an earplug, and; an aromatic material,
Whereby, upon manually adjusting the length of the head strap, the essentially rigid protrusion applies pressure on the user's glabella.

\* \* \* \* \*